United States Patent
Takayanagi et al.

(10) Patent No.: US 9,899,112 B2
(45) Date of Patent: Feb. 20, 2018

(54) PARTICLE BEAM THERAPY SYSTEM, RIDGE FILTER, AND METHOD OF MAKING RIDGE FILTER

(71) Applicants: Hitachi, Ltd., Tokyo (JP); NATIONAL UNIVERSITY CORPORATION HOKKAIDO UNIVERSITY, Sapporo-shi, Hokkaido (JP)

(72) Inventors: Taisuke Takayanagi, Tokyo (JP); Shinichiro Fujitaka, Tokyo (JP); Chihiro Nakashima, Tokyo (JP); Tomoki Murata, Tokyo (JP); Taeko Matsuura, Sapporo (JP); Naoki Miyamoto, Sapporo (JP); Kikuo Umegaki, Sapporo (JP); Yuichi Hirata, Sapporo (JP)

(73) Assignees: Hitachi, Ltd., Tokyo (JP); National University Corporation Hokkaido University, Hokkaido (JP)

( * ) Notice: Subject to any disclaimer, the term of this patent is extended or adjusted under 35 U.S.C. 154(b) by 0 days.

(21) Appl. No.: 15/437,826

(22) Filed: Feb. 21, 2017

(65) Prior Publication Data
US 2017/0243665 A1    Aug. 24, 2017

(30) Foreign Application Priority Data
Feb. 24, 2016   (JP) .................... 2016-032729

(51) Int. Cl.
*G21K 1/10* (2006.01)
*G21K 5/04* (2006.01)
*H05H 13/04* (2006.01)

(52) U.S. Cl.
CPC .............. *G21K 1/10* (2013.01); *G21K 5/04* (2013.01); *H05H 13/04* (2013.01)

(58) Field of Classification Search
CPC ............ G21K 1/10; G21K 1/02; G21K 1/025; G21K 1/04; G21K 1/043; G21K 1/046;
(Continued)

(56) References Cited

U.S. PATENT DOCUMENTS

2004/0000650 A1*   1/2004   Yanagisawa ......... A61N 5/1042
                                                    250/492.3
2004/0200983 A1*  10/2004   Fujimaki .................. A61N 5/10
                                                    250/492.3
(Continued)

FOREIGN PATENT DOCUMENTS

JP    2015-116284 A    6/2015

OTHER PUBLICATIONS

Uli Weber, et al., "Design and construction of a ripple filter for a smoothed depth dose distribution in conformal particle therapy", Phys. Med. Biol. 44, (1999), pp. 2765-2775.

*Primary Examiner* — David E Smith
(74) *Attorney, Agent, or Firm* — Mattingly & Malur, PC

(57) ABSTRACT

A structure configuring a ridge filter has line symmetry about a line vertical to a depth direction passing the center of the structure. A small structure obtained in such a way that the structure is divided by this line has a bilaterally asymmetric shape about a center line in an iterative direction, and has a point symmetric shape about an intersection between the center line in the iterative direction and the center line in the depth direction. Thicknesses in the iterative direction of an uppermost stream surface and a lowermost stream surface in the depth direction are equal to each other. The structure is configured so that a thick portion in the iterative direction of the uppermost stream surface and the lowermost stream surface is not present in the depth direction.

10 Claims, 14 Drawing Sheets

(58) Field of Classification Search
CPC .......... G21K 5/00; G21K 5/04; A61N 5/1042;
A61N 5/1077
See application file for complete search history.

(56) References Cited

U.S. PATENT DOCUMENTS

| | | | |
|---|---|---|---|
| 2010/0288946 A1* | 11/2010 | Honda | A61N 5/10 250/492.3 |
| 2012/0053389 A1* | 3/2012 | Chen | A61N 5/1042 600/1 |
| 2014/0018603 A1* | 1/2014 | Asaba | A61N 5/1031 600/1 |

* cited by examiner

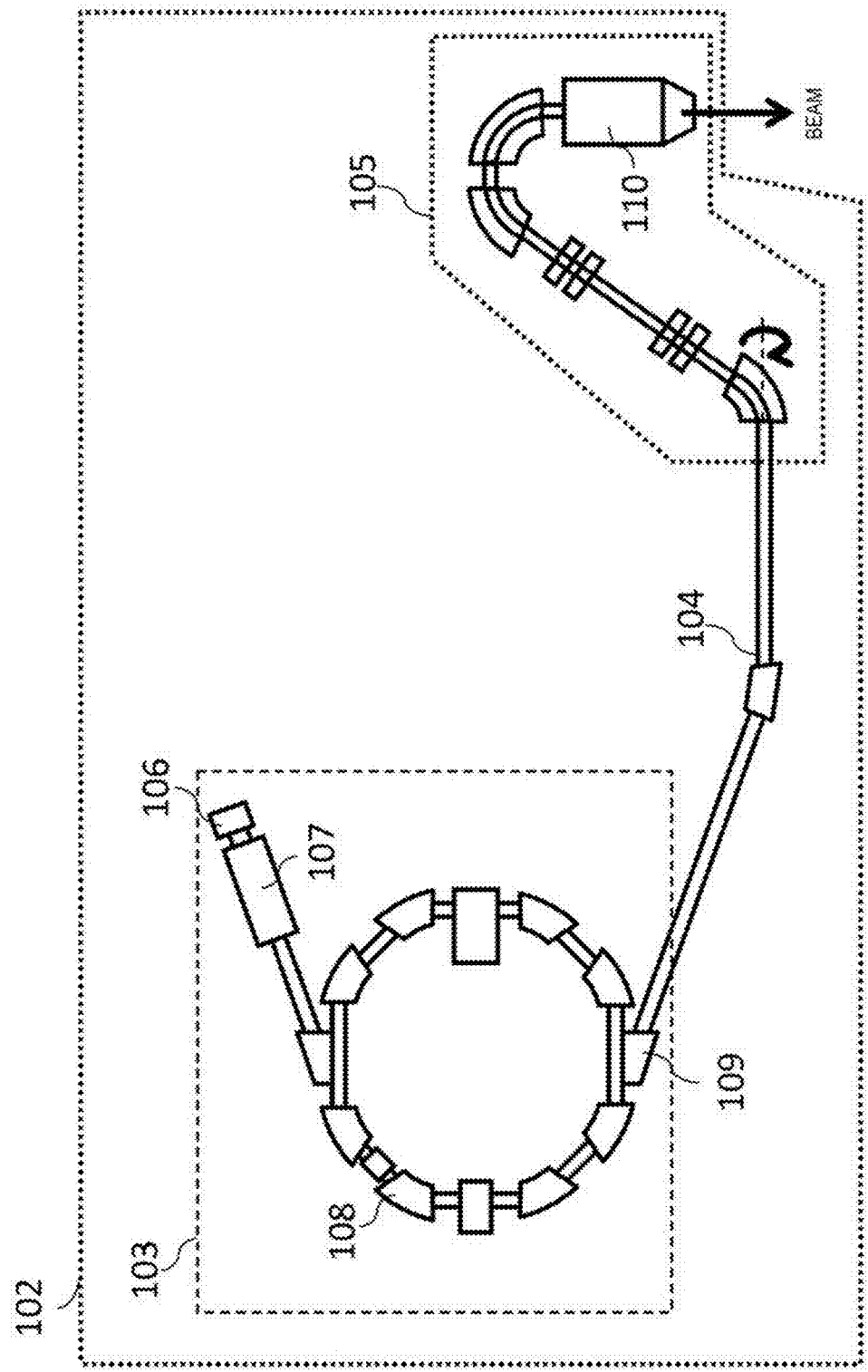
[Fig. 1]

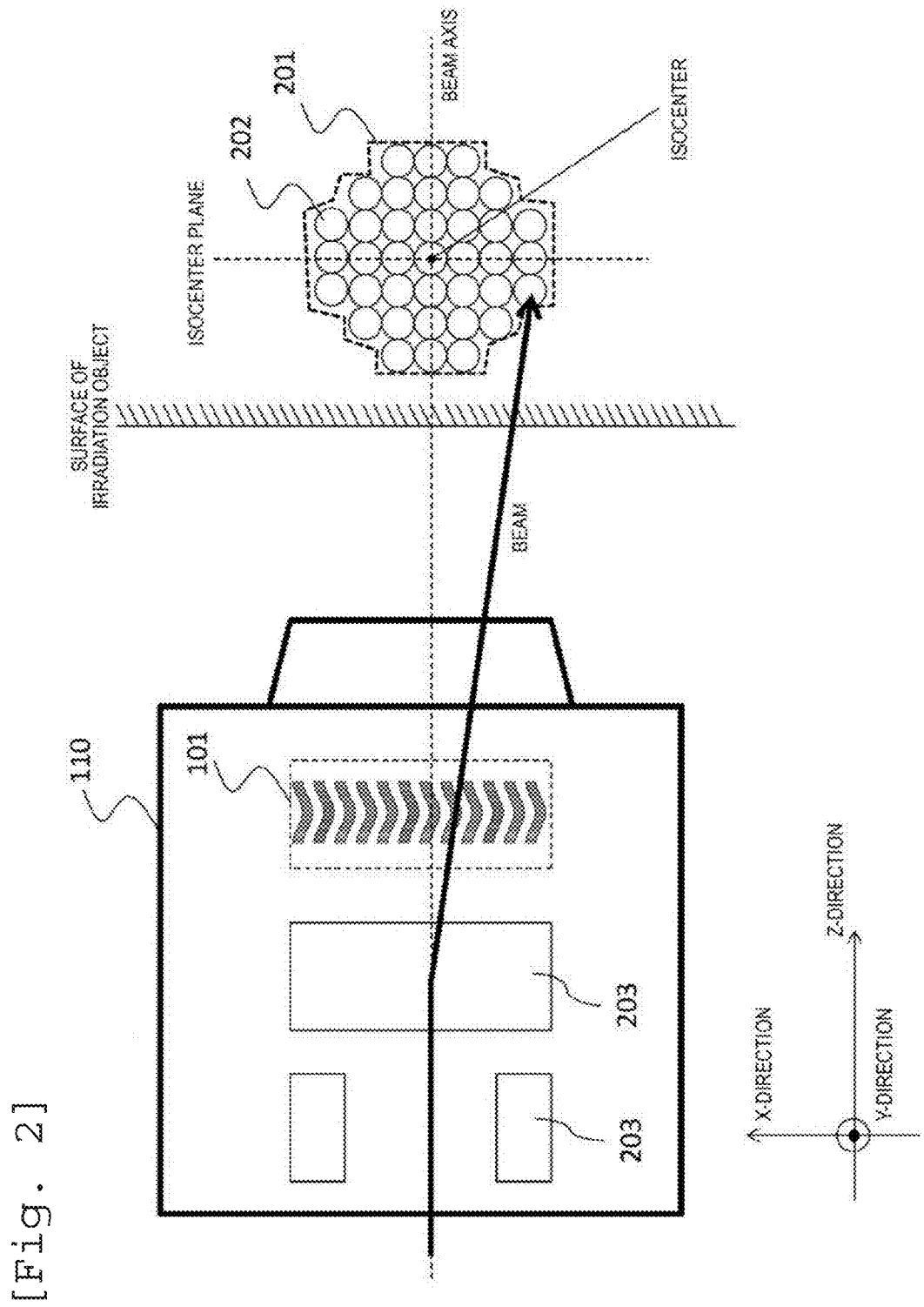

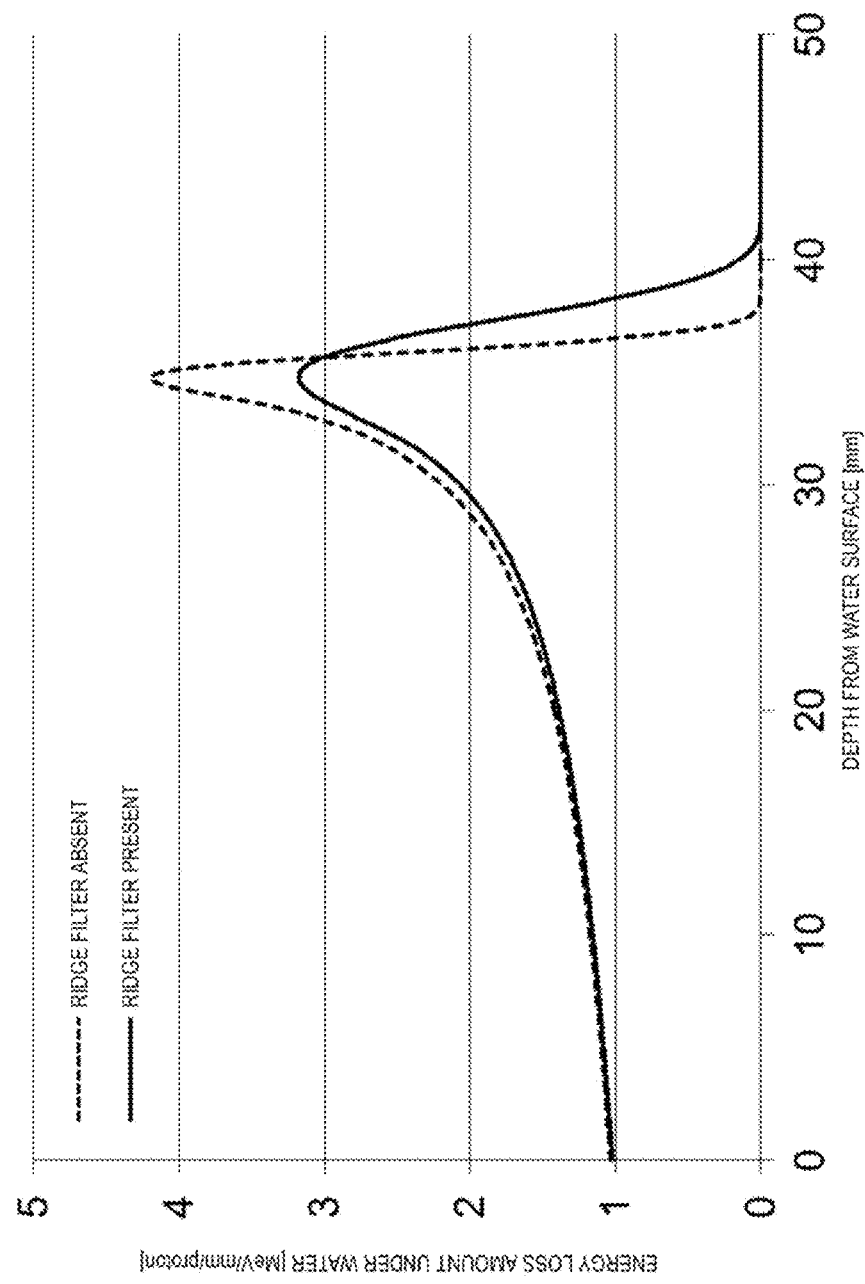
[Fig. 3]

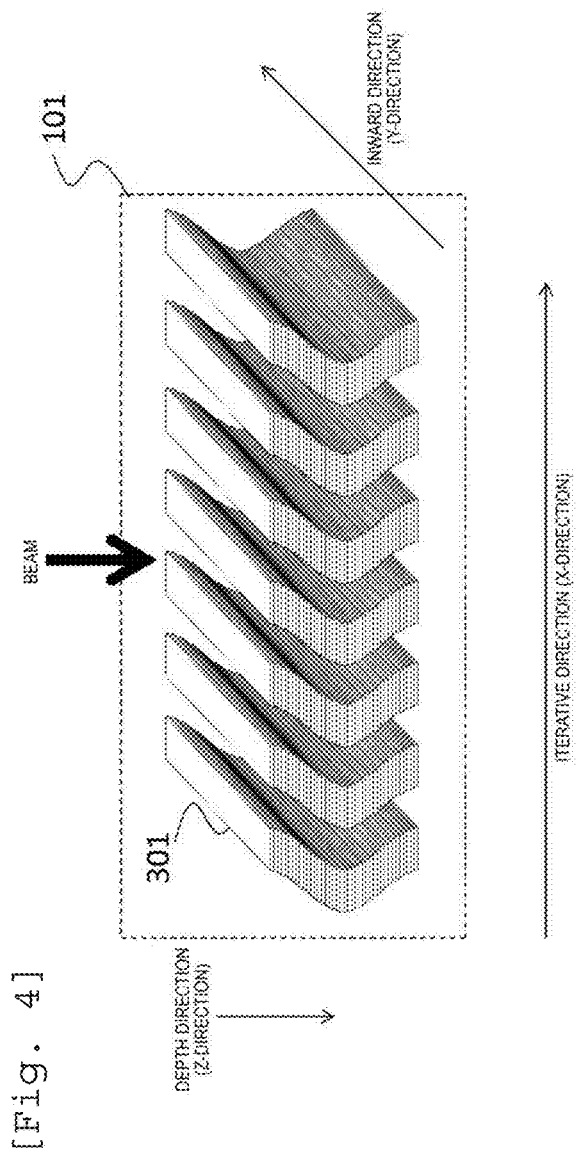

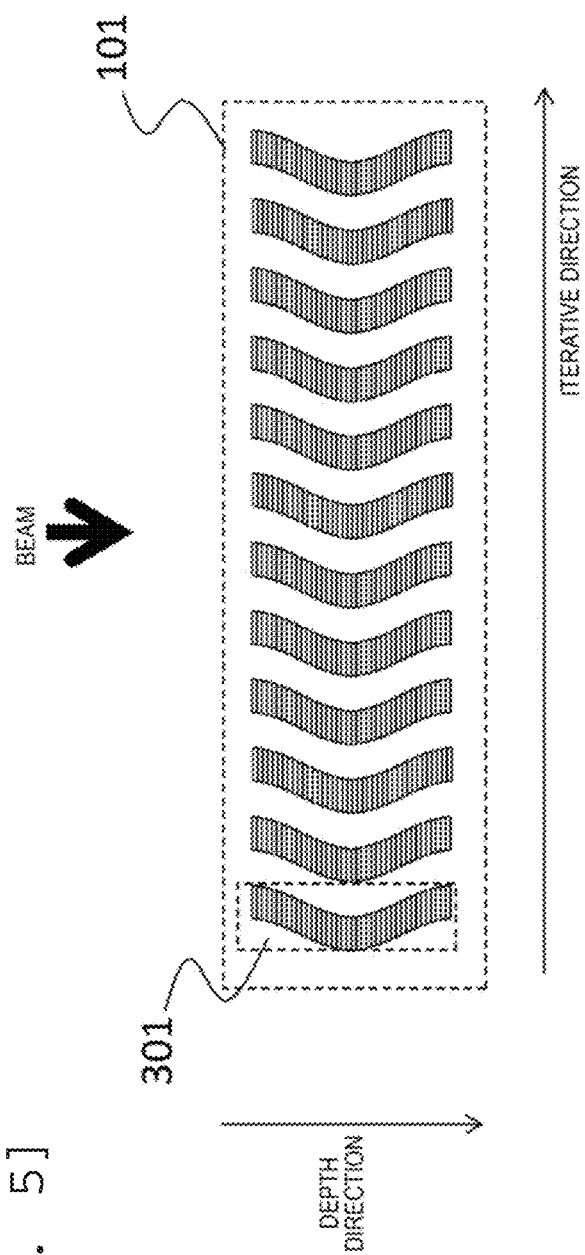

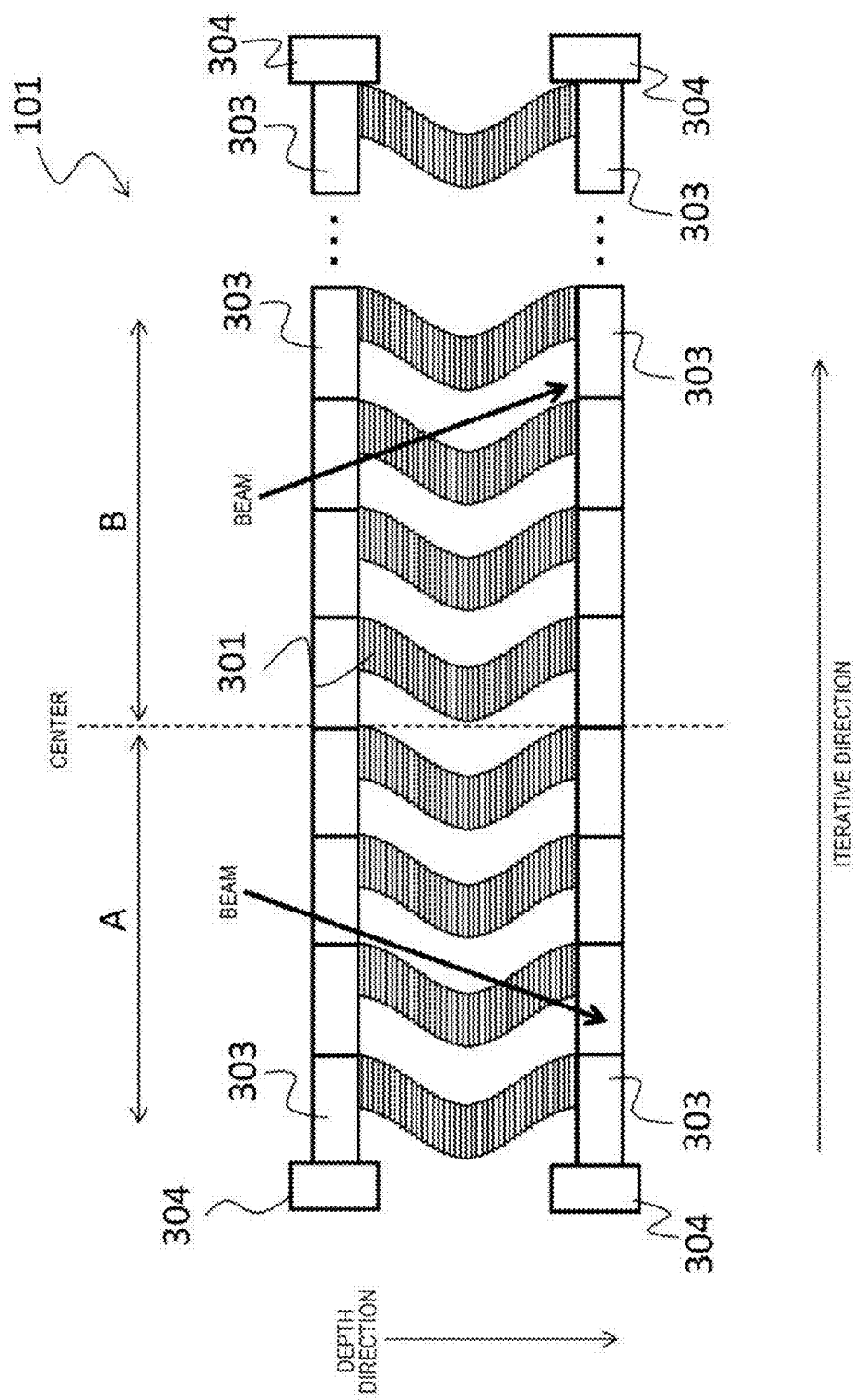
[Fig. 6]

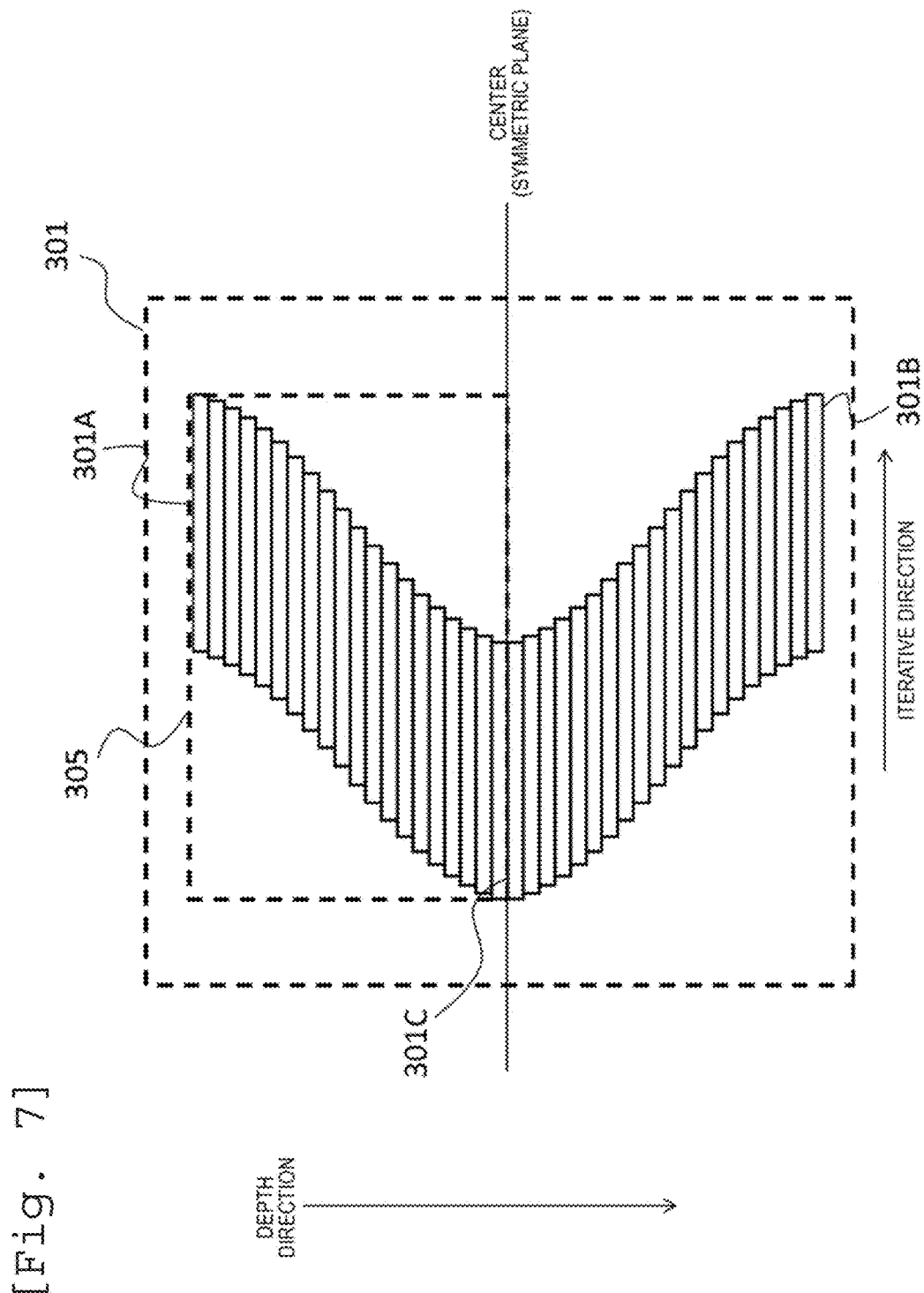
[Fig. 7]

[Fig. 8]
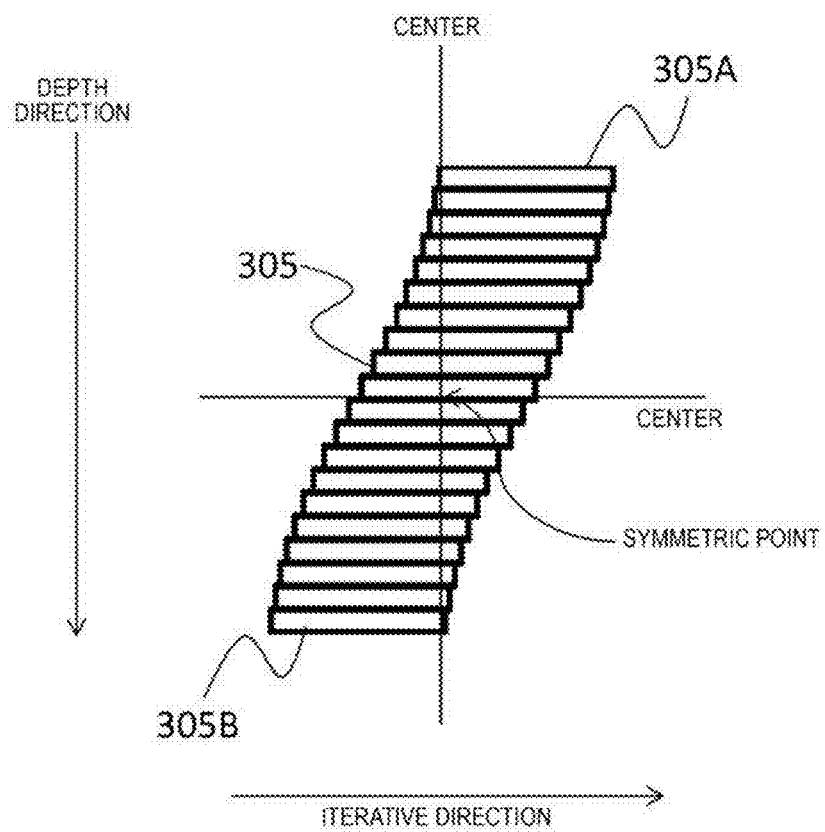
[Fig. 9]
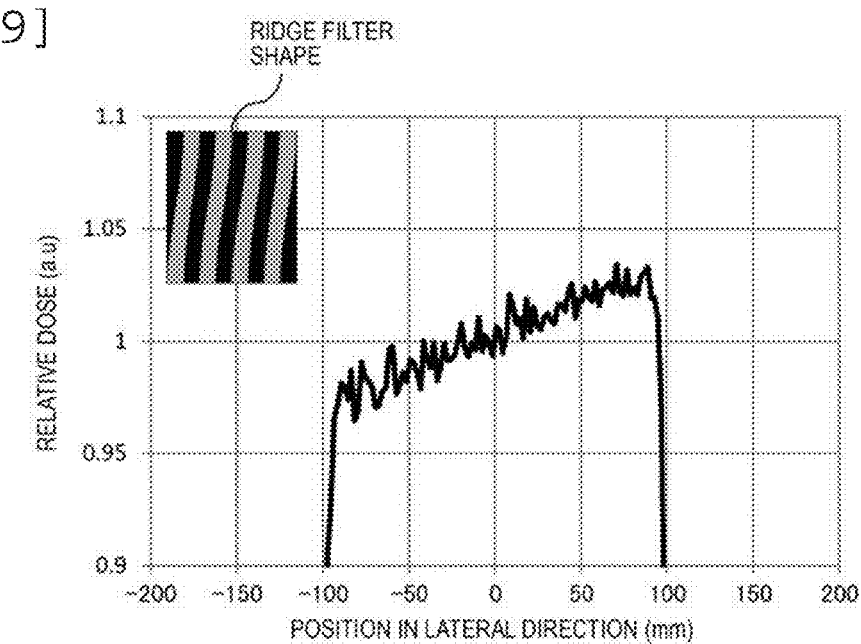

[Fig. 10]
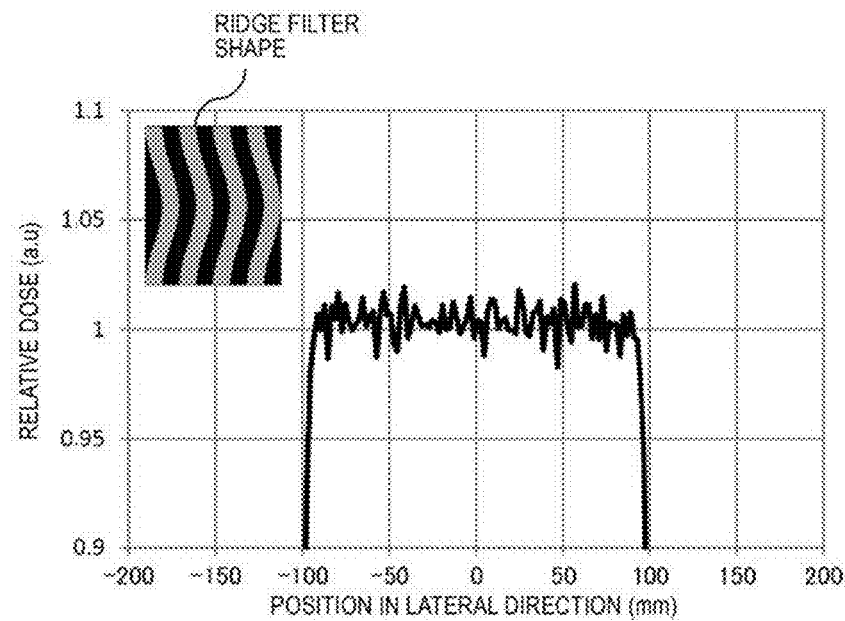
[Fig. 11]
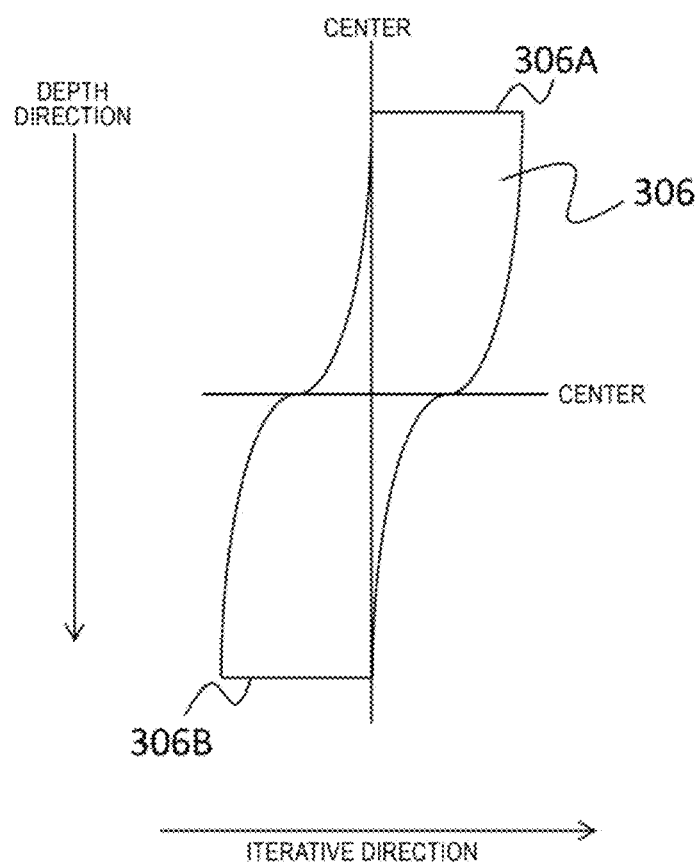

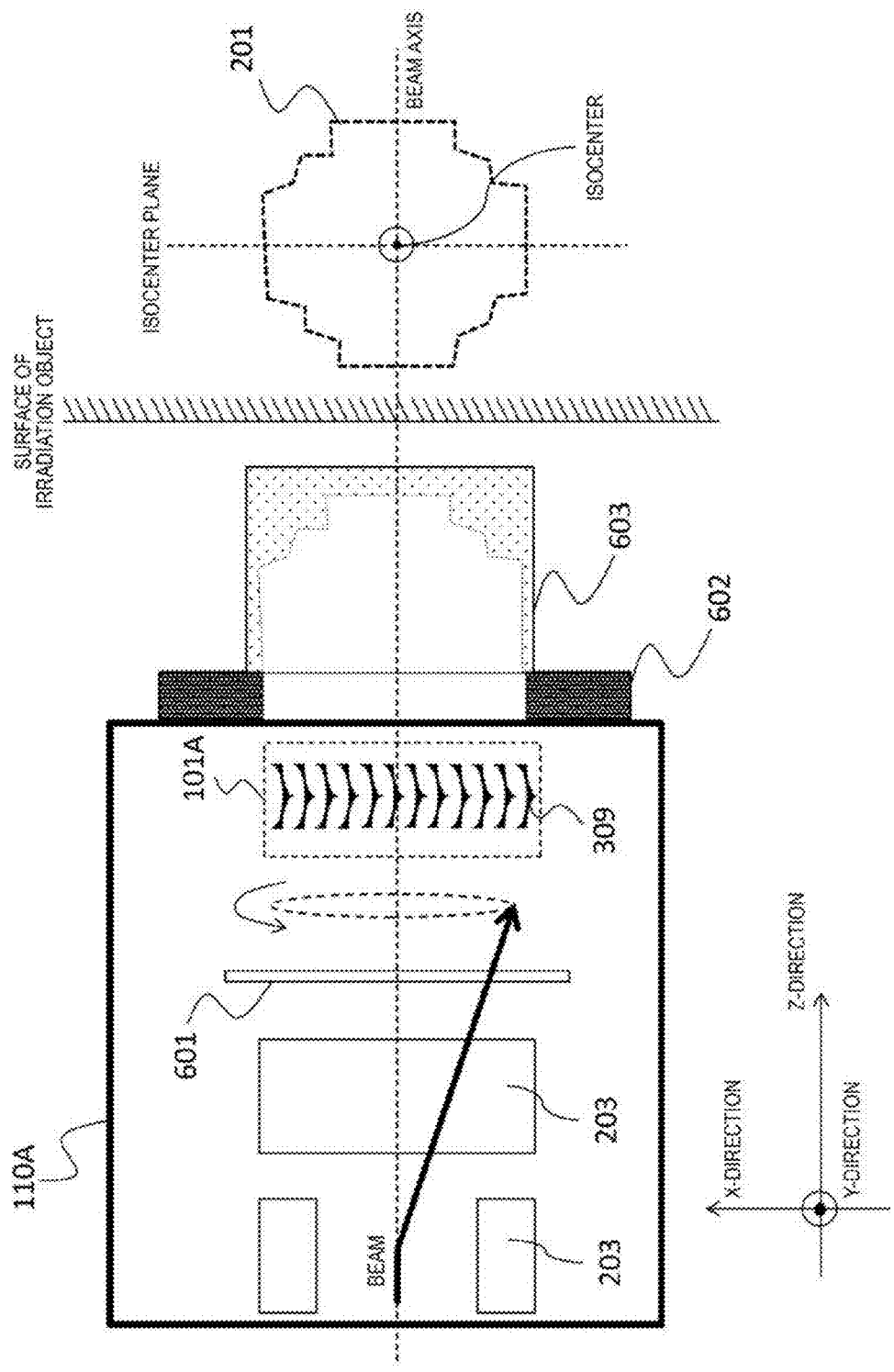
[Fig. 12]

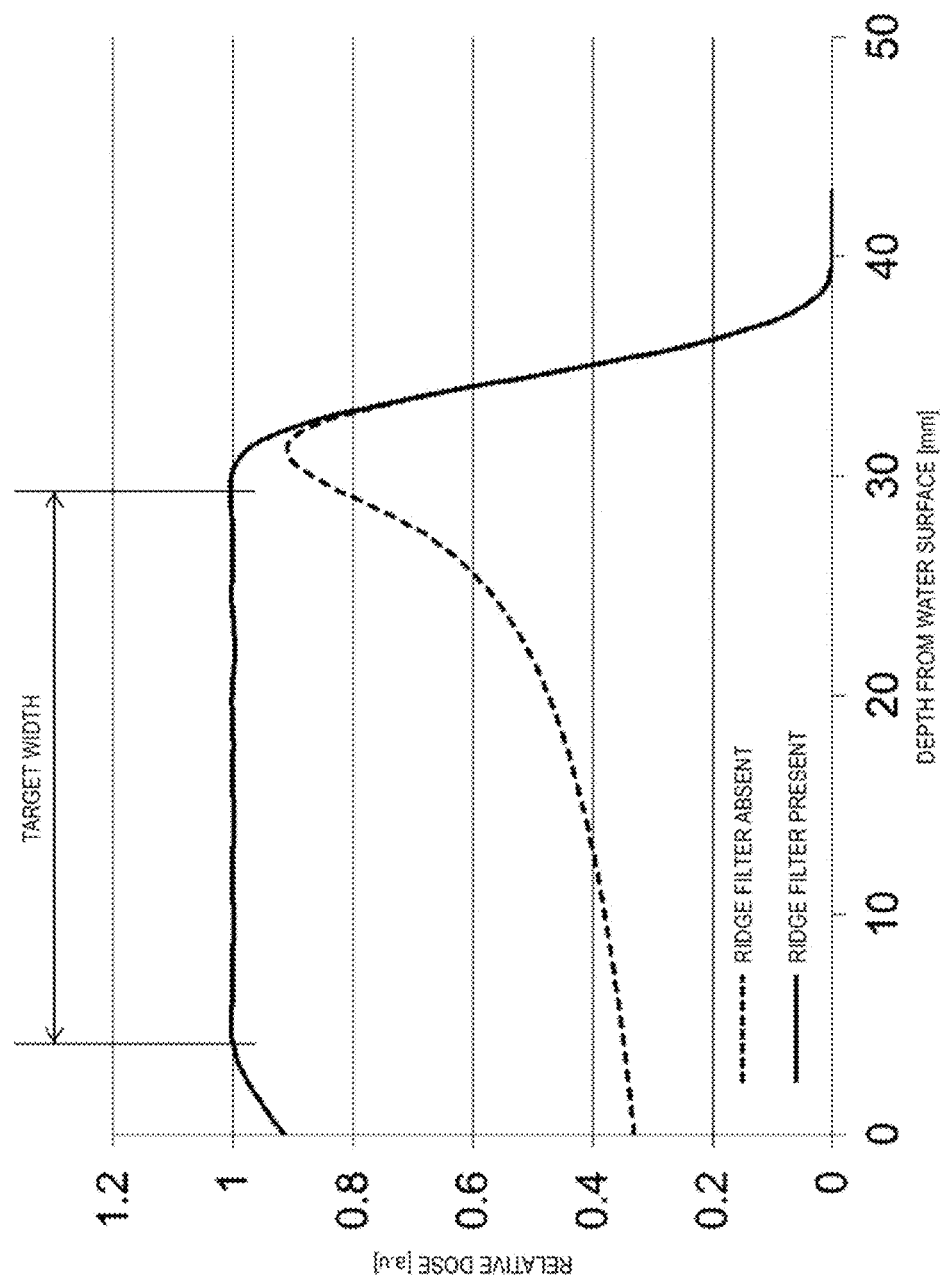
[Fig. 13]

[Fig. 14]
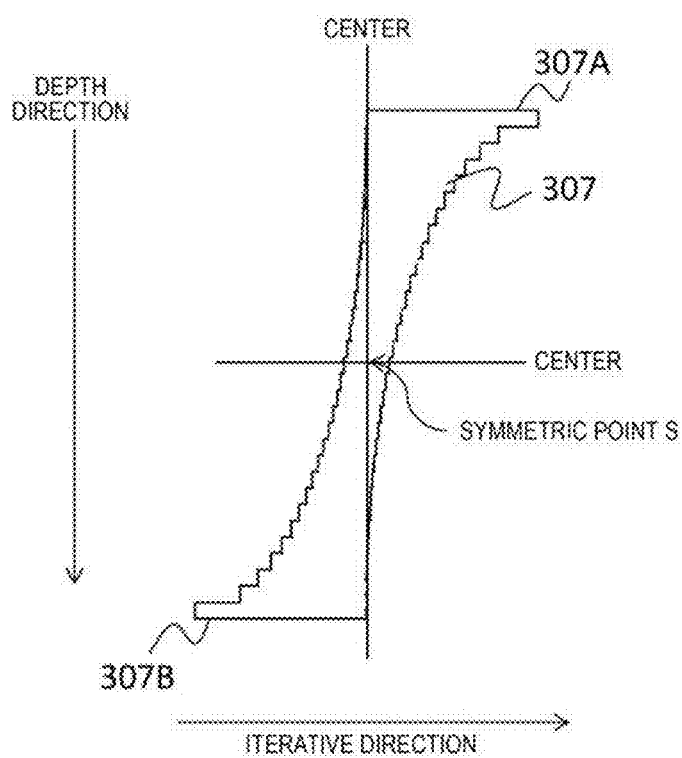
[Fig. 15]
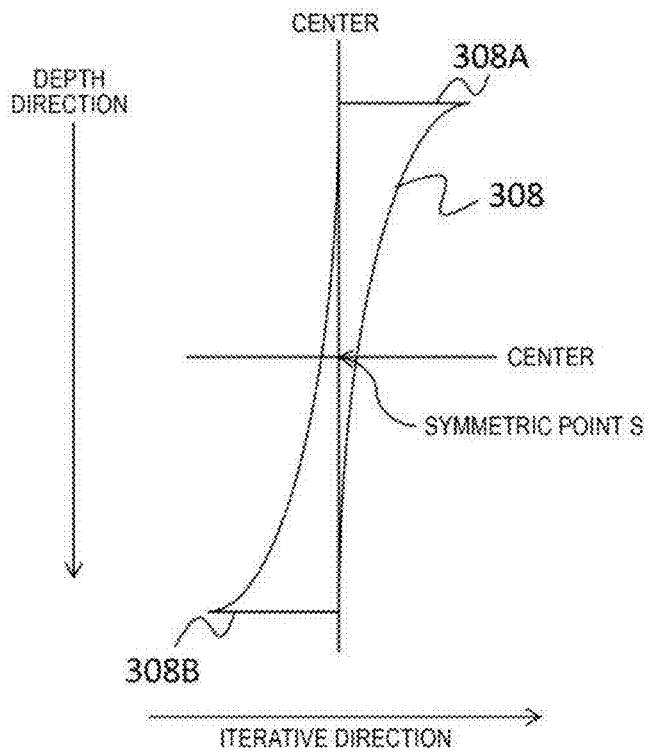

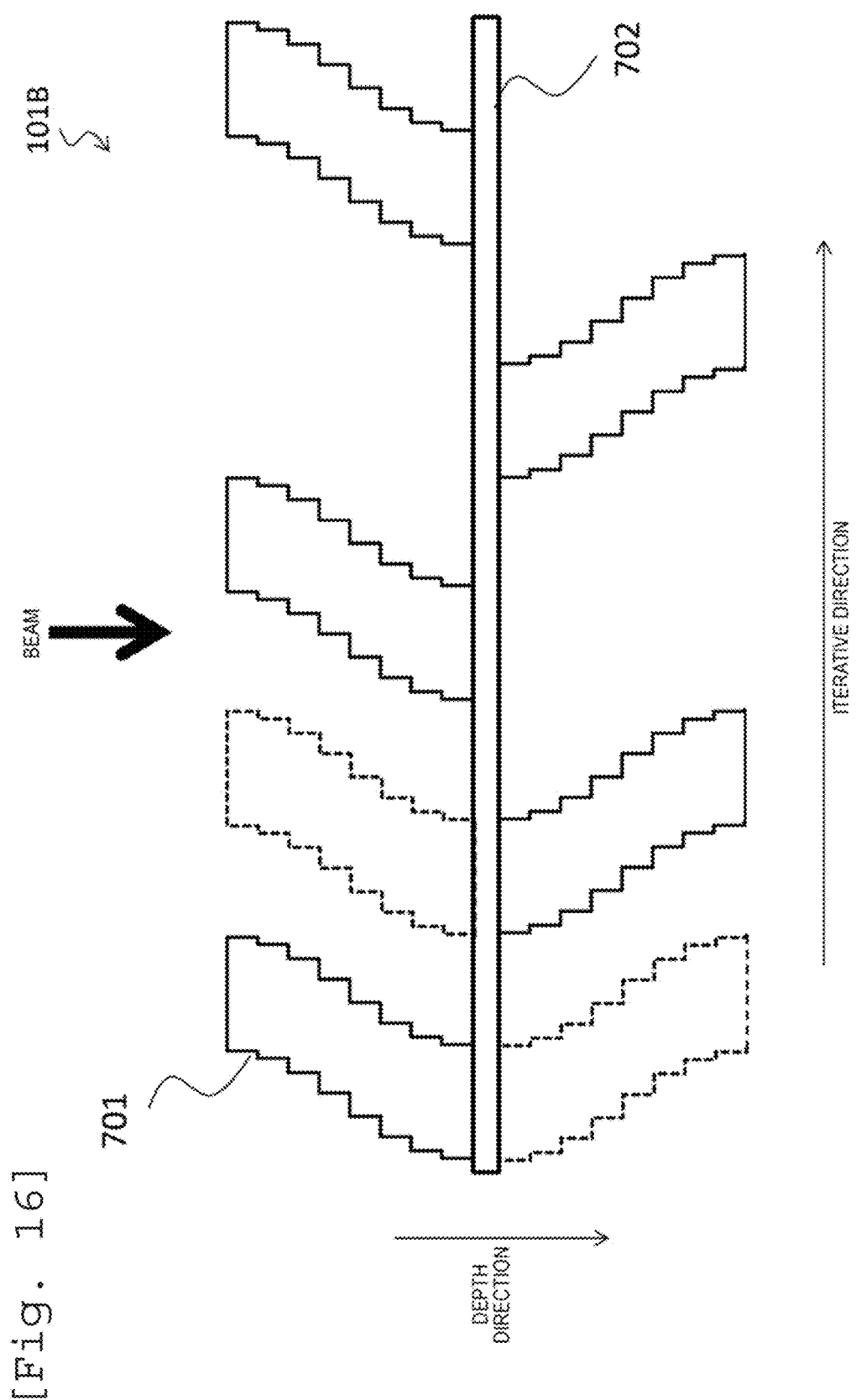
[Fig. 16]

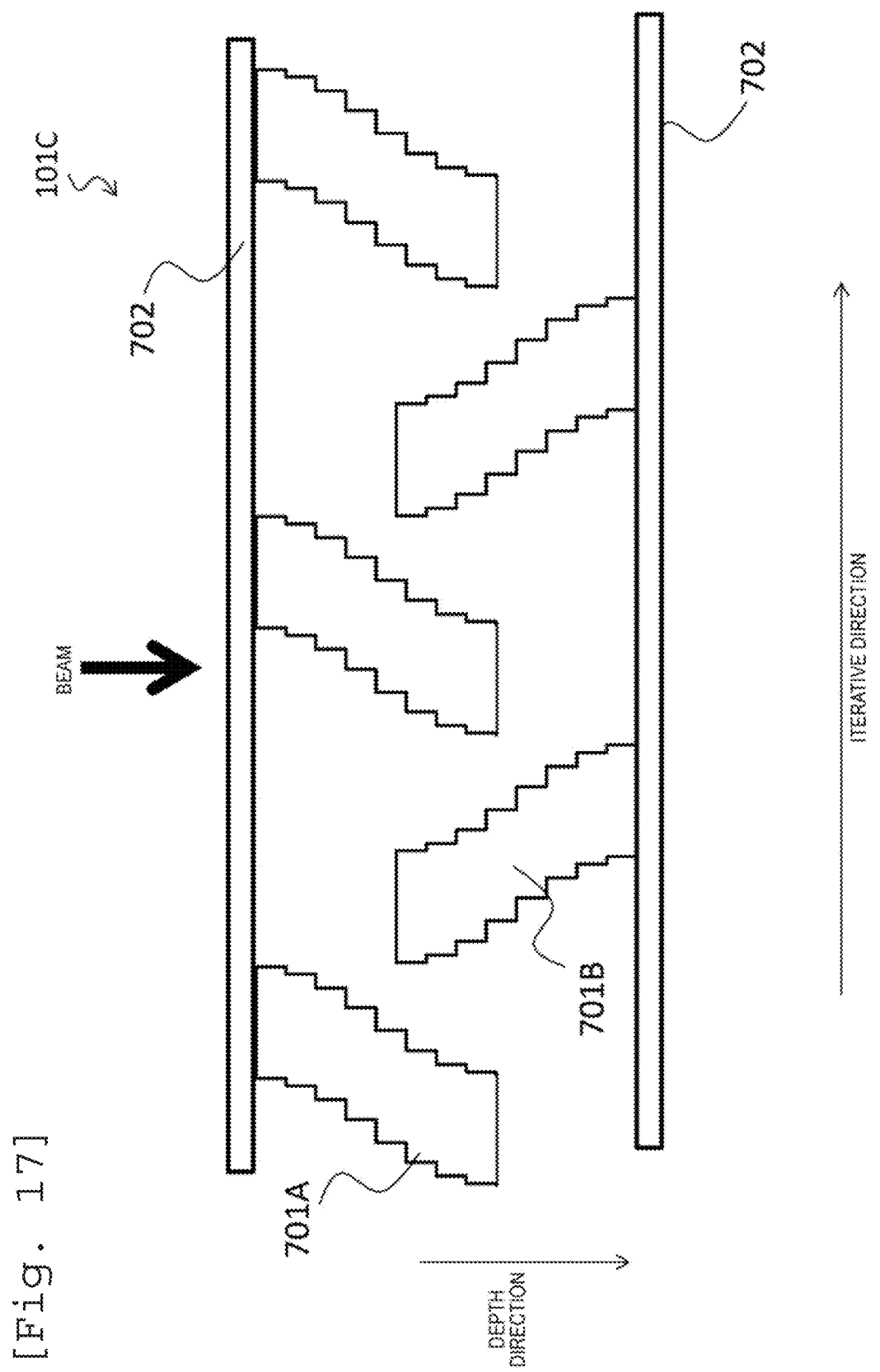
[Fig. 17]

PARTICLE BEAM THERAPY SYSTEM, RIDGE FILTER, AND METHOD OF MAKING RIDGE FILTER

TECHNICAL FIELD

The present invention relates to a particle beam therapy system, a ridge filter, and a manufacturing method of a ridge filter.

BACKGROUND ART

NPL 1 introduces a method of installing a ridge filter in a beam delivery system. The ridge filter in NPL 1 is configured so that bisymmetric mountain-like structures are arrayed in one line in a lateral direction.

In addition, PTL 1 discloses the following structure in order to sufficiently spread out a Bragg peak width. The structure includes a ridge filter provided with a function to disperse a range of abeam. The structure configuring the ridge filter has a point symmetric shape and a bilaterally asymmetric shape in an iterative direction of the structure. Thicknesses in the iterative direction of an uppermost stream surface and a lowermost stream surface in a depth direction are equal to each other. A thick portion in the iterative direction of the uppermost stream surface and the lowermost stream surface is not present in the depth direction.

CITATION LIST

Patent Literature

PTL 1: JP-A-2015-116284
NPL 1: U. Weber and G. Kraft, "Design and construction of a ripple filter for a smoothed depth dose distribution in conformal particle therapy", Phys. Med. Biol. 44 (1999) 2765-2775

SUMMARY OF INVENTION

Technical Problem

In particle beam therapy, a scanning irradiation method has been widely used. According to this scanning irradiation method, a target is considered as a divided micro region (hereinafter, referred to as a spot), and each spot is irradiated with a small size beam. If a predetermined dose is provided for a certain spot, beam irradiation is stopped, and the subsequent spot is scanned with the beam. In a case where the spot is scanned with the beam in a direction vertical (hereinafter, referred to as a lateral direction) to a beam traveling direction (hereinafter, referred to as a depth direction), a scanning magnet is used. If all spots in a certain depth are provided with the predetermined dose, the spots are scanned with the beam in the depth direction. In a case where the spots are scanned with the beam in the depth direction, energy of the beam is changed by using a method of changing an acceleration condition in an accelerator, or causing the beam to pass through a range shifter. Finally, all spots, that is, all targets are provided with a uniform dose.

In the spot scanning, as the spots are minutely arranged, an irradiation time tends to be lengthened, and a dose rate tends to decrease. Providing all targets with the uniform dose is called volume irradiation.

The beam for each spot forms a dose distribution called a Bragg curve in the depth direction. The Bragg curve has a peak (Bragg peak) in the vicinity of a range of the beam. At a position deeper than the Bragg peak, the dose rapidly decreases to substantially zero.

A depth where the Bragg peak is generated depends on energy of the beam incident on an irradiation object. As the beam has higher energy, the peak is generated at the deeper position. In addition, the beam for each spot spreads in a two-dimensional Gaussian distribution shape in the lateral direction. A Gaussian distribution 1σ, that is, a spot size is approximately 2 mm to 20 mm on an isocenter plane. As the beam has the higher energy, the spot size becomes smaller.

In a case where the Bragg curve has a sharp peak as in a heavy particle beam, it is necessary to arrange the spots at minute intervals in the depth direction. Consequently, the dose rate decreases, thereby causing a problem in that a treatment time is prolonged. In addition, in a case of a particle beam therapy system, it is necessary to prepare a large amount of beam energy. Therefore, much time and effort are required every day for quality assurance of the particle beam therapy system.

In order to solve this problem, the ridge filter introduced in NPL 1 has a function to spread out a Bragg peak width by dispersing a range of the beam in the Gaussian distribution shape. As the ridge filter is higher, a spread amount of the peak width increases, thereby enabling uniform dose distribution to be formed using a small number of spots. That is, a dose rate of the particle beam therapy system is improved. In addition, in the particle beam therapy system, owing to the spread peak width, a robust dose distribution can be formed in a range variation of the beam.

Here, an iterative interval in the lateral direction of the ridge filter needs to be minutely set to the same extent as the spot size. The reason is due to the following possibility. If the iterative interval is roughly set, the beams having different range losses are not sufficiently mixed together, and ripples are generated in the dose distribution in the lateral direction when the volume irradiation is performed, thereby resulting in a poor degree in dose uniformity.

Therefore, the particle beam therapy system for treating a small spot size has a problem in that the Bragg peak width cannot be sufficiently spread out by the ridge filter and the spot is less likely to be irradiated with the beam at high dose rate. The reason is as follows. According to the ridge filter having a structure introduced in NPL 1, a distal end portion having a minute iterative interval is thin, and thus, it becomes very difficult to process the structure which is high. In addition, since the distal end portion is thin, the particle beam therapy system has another problem in that the ridge filter, particularly, a distal end portion thereof tends to be damaged.

In order to solve these problems, PTL 1 discloses a ridge filter including a cross section having a shape similar to a parallelogram. The ridge filter includes a structure in which the mountain-like structure illustrated in NPL 1 is divided at the center and one side is vertically inverted. Therefore, although a range loss ratio is the same as that of the shape illustrated in NPL 1, processing work is easily carried out since a sharp portion is excluded.

If the beam is bent by the scanning magnet, the beam is obliquely incident on the ridge filter. In this case, an angle of the beam incident on the ridge filter depends on a position of the spot in the lateral direction. The ridge filter disclosed in PTL 1 has a bilaterally asymmetric structure. Accordingly, a range loss ratio of the beam in the ridge filter varies depending on the position of the spot. Therefore, the present inventors have found a problem that a uniform dose distribution cannot be formed for a target which is big in the lateral direction.

If a distance from the scanning magnet to the ridge filter is sufficiently lengthened in order to solve this problem, the beam used in scanning is set to be substantially parallel to the depth direction. Accordingly, this problem can be solved. However, there is still a problem in that the beam delivery system equipped with the scanning magnet and a rotating gantry have to increase in size and weight.

PTL 1 described above also discloses a structure arrangement in which structures configuring the ridge filter are alternately arrayed while being laterally inverted so that the overall ridge filter has a bisymmetric shape. According to this arrangement, it is conceivable that the uniform dose distribution can be obtained for the target even if the beam is obliquely incident on the ridge filter.

However, according to the structure arrangement disclosed in PTL 1, although the sharp portion is excluded, the present inventors have found the following problem. Particularly in a case where integral molding work is carried out for all of the structures by forming a narrow space in the ridge filter, work efficiency becomes poor. In addition, since a dimensional inspection cannot be performed on the narrow space portion, there is another problem in that the narrow space portion is less likely to be accurately controlled even in a case where the structures are manufactured.

The invention aims to provide a particle beam therapy system that can sufficiently spread out the Bragg peak width, that does not increase a size of a beam delivery system and a rotating gantry, and that has a small spot size which enables a uniform dose distribution to be formed in a target largely spreading in the lateral direction. The invention aims to further provide a ridge filter which is suitable for this particle beam therapy system and for which processing work is easily carried out, and a manufacturing method of the ridge filter.

Solution to Problem

In order to solve the above-described problems, the invention adopts configurations disclosed in Claims, for example. Although the invention includes a plurality of means for solving the above-described problems, as an example, there is provided a ridge filter for widening an energy distribution of a particle beam. The ridge filter has a first structure and a second structure which attenuate energy of the particle beam passing therethrough. When a particle beam incident direction in the ridge filter is defined as a depth direction, and one direction on a plane vertical to the particle beam incident direction is defined as an iterative direction, in the first structure, a first sectional shape on a plane including a straight line parallel to the depth direction and a straight line parallel to the iterative direction is a point symmetric shape in which the center of gravity of the first sectional shape functions as a symmetric point. When an uppermost stream side in the depth direction of the first sectional shape is set to a first side and a lowermost stream side in the depth direction of the first sectional shape is set to a second side, the first side and the second side are parallel to each other, and a length of the first side and the second side is longest in the iterative direction. A quadrangle having the first side and the second side is a parallelogram. The second structure has a shape in which the first structure is inverted by a plane vertical to the depth direction. A plurality of the first structures and the second structures are arranged in the iterative direction.

Advantageous Effects of Invention

According to the invention, it is possible to sufficiently spread out a Bragg peak width. Without increasing a size of a beam delivery system and a rotating gantry, it is possible to form a uniform dose distribution in a target largely spreading in the lateral direction.

BRIEF DESCRIPTION OF DRAWINGS

FIG. 1 is a view illustrating an overall configuration of a particle beam therapy system according to a first embodiment of the invention.

FIG. 2 is a schematic view of a beam delivery system according to the first embodiment of the invention.

FIG. 3 is a graph illustrating a dose distribution per one spot, which is formed by the beam delivery system employing a scanning irradiation method according to the first embodiment of the invention.

FIG. 4 is a schematic view of a partial configuration of a ridge filter according to the first embodiment of the invention.

FIG. 5 is a schematic sectional view on a plane vertical to an inward direction of the partial configuration of the ridge filter according to the first embodiment of the invention.

FIG. 6 is a schematic sectional view on a plane vertical to the inward direction of the ridge filter according to the first embodiment of the invention.

FIG. 7 is a schematic view illustrating an example of a structure configuring the ridge filter according to the first embodiment of the invention.

FIG. 8 is a schematic view illustrating an example of a small structure configuring the structure according to the first embodiment of the invention.

FIG. 9 is a schematic view illustrating an example of a dose distribution formed in a case where the ridge filter according to the first embodiment of the invention is replaced with a ridge filter in the related art.

FIG. 10 is a schematic view illustrating an example of a dose distribution formed by the ridge filter according to the first embodiment of the invention.

FIG. 11 is a schematic view illustrating another example of the small structure configuring the structure according to the first embodiment of the invention.

FIG. 12 is a schematic view of a beam delivery system according to a second embodiment of the invention.

FIG. 13 is a graph illustrating a dose distribution formed by a beam delivery system employing a scatterer irradiation method according to the second embodiment of the invention.

FIG. 14 is a schematic view illustrating an example of a small structure configuring a structure according to the second embodiment of the invention.

FIG. 15 is a schematic view illustrating another example of the small structure configuring the structure according to the second embodiment of the invention.

FIG. 16 is a schematic sectional view on a plane vertical to the inward direction of the ridge filter according to the first embodiment of the invention.

FIG. 17 is a schematic sectional view of another example on a plane vertical to the inward direction of the ridge filter according to a third embodiment of the invention.

DESCRIPTION OF EMBODIMENTS

Hereinafter, embodiments of a particle beam therapy system, a ridge filter, and a manufacturing method of the ridge filter will be described with reference to the drawings.

<First Embodiment>

A particle beam therapy system, a ridge filter, and a manufacturing method of the ridge filter according to a first embodiment of the invention will be described with reference to FIGS. 1 to 11. First, referring to FIG. 1, a configuration and an operation of the particle beam therapy system according to the first embodiment of the invention will be described. FIG. 1 is a view illustrating an overall configuration of the particle beam therapy system according to the first embodiment of the invention.

As illustrated in FIG. 1, the particle beam therapy system includes a proton beam irradiation device 102. The proton beam irradiation device 102 according to the present embodiment will be described as an example. However, the invention is also applicable to a heavy particle beam irradiation device using a particle (carbon beam or the like) whose mass is heavier than that of a proton.

As illustrated in FIG. 1, the proton beam irradiation device 102 has a proton beam generator 103, a proton beam transfer 104, and a rotating irradiation system 105. The rotating irradiation system 105 including a rotating gantry according to the present embodiment will be described as an example. However, a fixed-type irradiation device can also be employed.

In FIG. 1, the proton beam generator 103 has an ion source 106, a preaccelerator 107 (for example, linear accelerator), and a synchrotron 108. A proton ion generated by the ion source 106 is first accelerated by the preaccelerator 107. A proton beam (hereinafter, referred to as a beam) extracted from the preaccelerator 107 is accelerated with predetermined energy by the synchrotron 108. Thereafter, the beam is extracted from an extraction deflector 109 to a proton beam transfer 104. Finally, an irradiation object is irradiated with the beam passing through a rotating irradiation system 105.

The rotating irradiation system 105 has a rotating gantry (not illustrated) and a beam delivery system 110. The beam delivery system 110 installed in the rotating gantry rotates together with the rotating gantry. A portion of the proton beam transfer 104 is attached to the rotating gantry.

The present embodiment employs the synchrotron 108 as an acceleration device of the proton beam. However, a cyclotron or linear accelerator can be employed.

Next, details of the beam delivery system 110 will be described with reference to FIG. 2. FIG. 2 is a schematic view of the beam delivery system 110 employing a scanning irradiation method. In FIG. 2, according to the scanning irradiation method, a target 201 is divided into micro regions (spots) 202, and each spot 202 is irradiated with the beam. A range of the passing beam is dispersed in a Gaussian distribution shape. In order to spread out a Bragg peak width, a ridge filter 101 for widening an energy distribution of the beam is installed in the beam delivery system 110.

FIG. 3 is a conceptual diagram illustrating an underwater Bragg curve of the proton beam per one spot which passes through the ridge filter 101. In FIG. 3, in the particle beam therapy system according to the present embodiment, the spread Bragg peak width can widen an interval between the spots in a depth direction (Z-direction in FIG. 2), thereby enabling beam irradiation at high dose rate.

According to the scanning irradiation method, if a certain spot 202 is provided with a predetermined dose, the irradiation is stopped, and a subsequently predetermined spot 202 is scanned with the beam. In order to perform beam scanning in a lateral direction (X-direction and Y-direction in FIG. 2), a scanning magnet 203 mounted on the beam delivery system 110 is used.

If all of the spots 202 present up to a certain depth are provided with the predetermined dose, the beam delivery system 110 performs the beam scanning in the depth direction. The beam scanning in the depth direction is performed by changing an acceleration condition in the synchrotron 108 or by changing energy of the beam by means of a method of causing the beam to pass through a range shifter (not illustrated) mounted on the beam delivery system 110.

The above-described procedure is repeatedly performed, thereby finally forming the uniform dose distribution in the entire target 201. The dose distribution in the lateral direction of the beam for each spot 202 spreads in a Gaussian distribution shape of $1\sigma=2$ mm to 20 mm on an isocenter plane. According to the present embodiment, a straight line through which the center of the beam passes in a state where the scanning magnet 203 is not excited is defined as a beam axis. In addition, an intersection between a rotation axis of the rotating irradiation system 105 and the beam axis is defined as an isocenter.

Next, details of the ridge filter 101 will be described with reference to FIGS. 4 to 6. FIG. 4 illustrates a schematic view of a partial configuration of the ridge filter 101. FIG. 5 illustrates a schematic view of a cross section of the partial configuration of the ridge filter 101 on a plane vertical to an inward direction. FIG. 6 illustrates a schematic cross section of the ridge filter 101 on a plane vertical to an iterative direction.

As illustrated in FIGS. 4 and 5, when a direction the same as a beam incident direction is defined as the depth direction (the same as a Z-direction in FIG. 2), one direction of the ridge filter 101 on a plane vertical to the beam incident direction is defined as the iterative direction (the same as an X-direction in FIG. 2), and another direction is defined as the inward direction (the same as a Y-direction in FIG. 2), the ridge filter 101 has a structure in which a plurality of structures 301 are arranged in the iterative direction. In the inward direction, the structure has a shape in which a surface such as an uppermost stream surface 301A extends.

In addition, as illustrated in FIG. 5, in the ridge filter 101, a sectional shape on a plane vertical to the inward direction is the same shape as a sectional shape (third sectional shape) of an air layer (hereinafter, referred to as a gap) formed between a certain structure 301 and the adjacent structure 301, and a sectional shape (second sectional shape) of the structure 301 itself.

In addition, as illustrated in FIG. 6, the structure 301 is in contact with a base portion 303 on the uppermost stream surface 301A side and a lowermost stream surface 301B side in the depth direction. In addition, the base portion 303 is fixed in a form in which a plurality of the base portions 303 are pinched by fixing portions 304 in the iterative direction. The fixing portions 304 may fix the base portions 303 in the inward direction, or may fix the base portions 303 in both directions of the iterative direction and the inward direction.

According to the present embodiment, the structures 301 of the ridge filter 101 are individually processed and manufactured one by one, and all of the structures 301 are pinched and fixed by the fixing portions 304. However, a configuration may be adopted in which a metal mold is prepared so as to process and manufacture an integrally molded product of all structures and base portions by means of casting or injection molding. Another configuration may be adopted in which only the structure 301 portion is formed by a 3D printer or the structure 301 is integrally formed including the base portion 303 and the fixing portion 304. Even according to these configurations, it is possible to obtain the same advantageous effect as that according to the present embodiment.

Next, details of the structure 301 configuring the ridge filter 101 will be described with reference to FIG. 7. FIG. 7 illustrates a schematic view of the structure 301 configuring the ridge filter 101.

In the structure 301, a sectional shape on a plane vertical to the inward direction is line symmetry about a line vertical to the depth direction which passes through the center of the structure 301. In addition, even if the structure 301 is vertically inverted by a plane vertical to the depth direction, the structure 301 has the same shape. The structure 301 is divided into two small structures 305 by the vertical plane. In the small structures 305, an upstream side in the depth direction is a first structure, and a lower side is a second structure.

In addition, the structure 301 is formed so that thicknesses in the iterative direction of the uppermost stream surface 301A, the lowermost stream surface 301B, and an intermediate surface 301C in the depth direction are equal to each other. The structure is configured so that a thick portion in the iterative direction from the three surfaces (the uppermost stream surface 301A, the lowermost stream surface 301B, and the intermediate surface 301C) is not present in the depth direction.

Next, details of the small structure 305 configuring the structure 301 will be described with reference to FIG. 8. FIG. 8 illustrates a schematic view of the small structure 305 configuring the structure 301.

As illustrated in FIG. 8, the small structure 305 has a step shape and an inverted step shape in the depth direction, and is formed so as to spread out the Bragg peak width.

In addition, in the small structure 305, a sectional shape on a plane vertical to the inward direction is a bilaterally asymmetric shape about the center line in the iterative direction, and is a point symmetric shape about an intersection S (center of gravity) between the center line in the iterative direction and the center line in the depth direction. The small structure 305 has a shape having no mountain-like sharp portion (distal end portion or apex) in the depth direction.

Furthermore, in the small structure 305, the thicknesses (lengths) in the iterative direction of the uppermost stream surface 305A and the lowermost stream surface 305B in the depth direction are equal to each other. In addition, the structure is configured so that a thick (long) portion in the thickness (length) in the iterative direction from the uppermost stream surface 305A and the lowermost stream surface 305B is not present in the depth direction.

The ridge filter 101 according to the present embodiment includes a plurality of the structures 301 in which the two small structures 305 satisfying the above-described structure are combined with each other. Accordingly, a range of the beam can be dispersed in the Gaussian distribution shape, and the Bragg peak width can be spread out.

In an example of the small structure 301 in FIG. 8, the number of steps is 20 for the convenience of illustration. However, without being limited to 20 steps, the number of steps can be appropriately changed in accordance with performance required for the ridge filter.

As described above, the sectional shape on the plane vertical to the inward direction of the small structure 305 has the bilaterally asymmetric shape. Therefore, if the ridge filter 101 is configured to include a structure having the same shape as that of the small structure 305 instead of the structure 301 illustrated in FIG. 5, in a case where a distance from a scanning magnet to a target is short and the beam is obliquely incident on the ridge filter 101, a range loss ratio of the beam in the ridge filter 101 varies depending on a spot position.

Therefore, even if each spot of the target is provided with an equal dose in the lateral direction, the uniform dose distribution cannot be obtained as illustrated in FIG. 9. In this case, in order to obtain the uniform dose distribution, it becomes necessary to lengthen the distance from the scanning magnet to the ridge filter so that the beam is incident on the ridge filter while being parallel to the depth direction. FIG. 9 is a view illustrating an example of the dose distribution in a case of using the ridge filter having a structure in the related art.

However, as illustrated in FIG. 7, the structure 301 according to the present embodiment has a structure in which another small structure 305 which is vertically inverted by a plane vertical to the depth direction is disposed downstream of the small structure 305. Accordingly, a change in range loss depending on the spot position is offset. That is, even in a case where the beam is obliquely incident on the ridge filter 101 in the depth direction, the uniform dose distribution can be formed for the target in the lateral direction as illustrated in FIG. 10. FIG. 10 is a view illustrating an example of the dose distribution in a case of using the ridge filter 101 having a structure according to the present embodiment.

Therefore, the distance from the scanning magnet to the ridge filter can be shortened. Without increasing the size and the weight of the beam delivery system equipped with the scanning magnet and the rotating gantry, the uniform dose distribution can be formed for the target which is big in the lateral direction.

Next, a manufacturing method of the ridge filter 101 having this structure will be described.

A material of the small structure 305 configuring the structure 301 of the ridge filter 101 needs to absorb energy by restraining the beam from being scattered. Accordingly, metal such as aluminum or copper, and an acrylonitrile butadiene styrene (ABS) resin may be used.

The required number of the structures 301 is manufactured in such a way that an ingot (material mass) is cut by using a lathe or a milling machine. As another method, a plurality of the structures 301 can be formed using a 3D printer, or a plurality of plates formed of the above-described materials are formed so as to be stacked on each other in the depth direction.

As a manufacturing condition of the structure 301, it is possible to employ a general condition. It is conceivable to form the small structure 305 having no sharp portion of the structure 301, that is, the small structure 305 in which a sectional shape on a plane vertical to the inward direction is line symmetry about a line vertical to the depth direction which passes through the center of the structure 301 and the structure 301 is divided by the vertical line. In this case, a structure is configured so that the small structure 305 has a bilaterally asymmetric shape about the center line in the iterative direction, a point symmetric shape about the intersection S between the center line in the iterative direction and the center line in the depth direction, the thicknesses in the iterative direction of the uppermost stream surface 301A and the lowermost stream surface 301B in the depth direction are equal to each other, and a thick portion in the iterative direction of the uppermost stream surface 305A and the lowermost stream surface 305B is not present in the depth direction. In order to employ this structure, the small structure 305 is manufactured in such a way that the above-described ingot formed of aluminum, copper, or ABS is cut and processed, or is formed of these materials by using the 3D printer.

The base portion 303 is manufactured by being simultaneously cut and processed together with the structure 301, or is integrally formed by the 3D printer. Alternatively, after the structure 301 is manufactured by the cutting process or the 3D printer, the separately manufactured base portion 303 is attached to the uppermost stream surface 301A and the lowermost stream surface 301B, thereby brining the base portion 303 into contact with the structure 301. It is desirable that a material of the base portion 303 and the fixing portion 304 is the same as that of the structure 301.

After a plurality of the structures 301 including this base portion 303 are manufactured, a plurality of the structures are arranged in the iterative direction. In this state, the base portion 303 is fixed by the fixing portion 304, thereby manufacturing the ridge filter 101. Alternatively, a plurality of the structures 301, the base portions 303, and the fixing portions 304 may be integrally formed by the 3D printer.

Next, an advantageous effect according to the present embodiment will be described.

As described above, according to the first embodiment of the particle beam therapy system, the ridge filter, and the manufacturing method of the invention, there is provided the ridge filter 101 having a function to disperse a range of the beam. The structure 301 configuring the ridge filter 101 is the line symmetry about the line vertical to the depth direction which passes through the center of the structure 301. The small structure 305 obtained in such a way that the structure 301 is divided by the line has the bilaterally asymmetric shape about the center line in the iterative direction, and the point symmetric shape about the intersection between the center line in the iterative direction and the center line in the depth direction. The thicknesses in the iterative direction of the uppermost stream surface 301A and the lowermost stream surface 301B in the depth direction are equal to each other. The structure is configured so that the thick portion in the iterative direction from the uppermost stream surface 301A and the lowermost stream surface 301B is not present in the depth direction.

That is, in the small structure 305, a sectional shape on the plane including the straight line parallel to the depth direction and the straight line parallel to the iterative direction is the point symmetric shape in which the center of gravity of the sectional shape functions as the symmetric point. When an uppermost stream side in the depth direction of the sectional shape is set to a first side and a lowermost stream side is set to a second side, the first side and the second side are parallel to each other, and the length of the first side and the second side is longest in the iterative direction. The quadrangle having the first side and the second side is the parallelogram.

Accordingly, since the spot interval can be widened in the depth direction, the amount of the beam energy required for the volume irradiation can be reduced, and time and effort can be reduced in assuring the quality of the particle beam therapy system. Furthermore, since the ridge filter is less likely to be damaged, an occupancy rate of the particle beam therapy system is improved.

In addition, in the structure 301, the thicknesses in the iterative direction of the uppermost stream surface 301A, the lowermost stream surface 301B, and the intermediate surface 301C in the depth direction are equal to each other. The thick portion in the iterative direction from the three surfaces is not present in the depth direction. Furthermore, in the structure 301 configuring the ridge filter 101, the sectional shape on the plane vertical to the inward direction is the same shape even if the structure 301 is vertically inverted by the plane vertical to the depth direction. Therefore, even in a case of a small spot size, it is possible to improve a dose rate without causing a poor degree in dose uniformity. In addition, the spot interval can be widened in the depth direction, and the amount of the beam energy required for the volume irradiation can be reduced. Furthermore, the ridge filter is less likely to be damaged.

In addition, the structure 301 is a structure in which another small structure 305 which is vertically inverted by the plane vertical to the depth direction is disposed downstream of the small structure 305. Accordingly, a change in range loss depending on the spot position is offset. That is, even in a case where the beam is obliquely incident on the ridge filter 101 in the depth direction, the uniform dose distribution can be formed for the target in the lateral direction as illustrated in FIG. 10.

The structure 301 of the ridge filter 101 is a structure having no mountain-like sharp portion. Accordingly, it is possible to manufacture a structure whose iterative interval is minute and which is high. Therefore, since the ridge filter 101 including this structure 301 is used and the particle beam therapy system using the scanning irradiation method is used, even in a case of a small spot size, it is possible to improve a dose rate without causing a poor degree in dose uniformity.

In addition, since the structure 301 of the ridge filter 101 has no sharp portion, the structure 301 is easily processed. Accordingly, it is easy to manufacture the structure 301, and it is possible to reduce the cost needed to manufacture the ridge filter. Therefore, it is possible to inexpensively provide the particle beam therapy system. Furthermore, it is very easy to raise the height of the distal end portion of the ridge filter 101 in the beam traveling direction (depth direction), and the Bragg peak width can be easily spread out. Accordingly, it is not necessary to install a thick range shifter in order to spread out the Bragg peak width. Therefore, it is possible to maintain a minute beam size.

In addition, in the ridge filter 101, the sectional shape of the structure 301 portion and the sectional shape of the gap are the same shape on the plane vertical to the inward direction. Accordingly, even if the iterative interval is minute and the structure is high, a space is sufficiently secured when the structure 301 portion is formed, and strength of the structure 301 is sufficiently secured. Therefore, it is possible to very accurately manufacture the structure 301. An advantageous effect can be obtained in that the dose rate can be improved without causing a poor degree in dose uniformity, even in a case of the small spot size.

In addition, the ridge filter 101 further has the base portions 303 which are respectively in contact with the structure 301 on the uppermost stream surface 301A or the lowermost stream surface 301B of the structure 301, and the fixing portions 304 which pinch a plurality of the base portions 303 in at least any one direction of the iterative direction and the inward direction. Therefore, when the ridge filter 101 is moved or rotated, it is possible to strongly restrain the portion of the structure 301 from being bent, and the irradiation can be more accurately performed. Accordingly, the ridge filter is suitably mounted on the rotating gantry. In addition, when the structures 301 are very accurately arrayed and fixed in the iterative direction, the structures 301 are sufficiently fixed in such a simple way that the structures 301 are pinched by the fixing portions 304 in the inward direction. Thus, it becomes easy to fix the structures 301, and it becomes easy to minutely adjust the structures 301. Accordingly, the structures 301 can be very accurately arranged in the iterative direction, the ridge filter can be excellently handled. Furthermore, since the base portions 303 are fixed by the fixing portions 304, the structure 301 has no burden. The structure 301 is much less likely to be damaged, thereby contributing to an improved occupancy rate of the particle beam therapy system.

As the small structure configuring the structure 301 of the ridge filter 101, without being limited to the structure having the step shape in the depth direction as illustrated in FIG. 8, it is possible to employ a structure (small structure 306) having a smooth shape in the depth direction as illustrated in FIG. 11.

The small structure 306 as illustrated in FIG. 11 also has the bilaterally asymmetric shape about the center line in the iterative direction, and the point symmetric shape about the intersection between the center line in the iterative direction and the center line in the depth direction. In the small structure 306, the thicknesses in the iterative direction of the uppermost stream surface 306A and the lowermost stream surface 306B in the depth direction are equal to each other. Furthermore, the thick portion in the iterative direction from the uppermost stream surface 306A and the lowermost stream surface 306B in the depth direction is not present. The structure has the same thickness.

The small structure 306 having this structure can also be manufactured by performing cutting and processing on the ingot formed of aluminum, copper, or ABS, or by using a method such as the 3D printer.

Even if the small structure configuring the structure of the ridge filter 101 is the small structure 306 as illustrated in FIG. 11, it is possible to obtain the same advantageous effect as that described above.

<Second Embodiment>

A second embodiment of the particle beam therapy system, the ridge filter, and the manufacturing method according to the invention will be described with reference to FIGS. 12 to 15. The thickness direction, the iterative direction, and the inward direction are the same as those in the first embodiment. In addition, an overall configuration of the particle beam therapy system according to the present embodiment is the same as that illustrated in FIG. 1.

The beam delivery system 110 according to the first embodiment employs the scanning irradiation method. However, even in a case where a wobbler irradiation method is employed, the same advantageous effect can be obtained. In the present embodiment, the wobbler irradiation method will be described with reference to FIGS. 12 and 13. FIG. 12 is a schematic view of a beam delivery system according to the present embodiment which employs the wobbler irradiation method. FIG. 13 is a graph illustrating a dose distribution formed by the beam delivery system according to the present embodiment.

As illustrated in FIG. 12, according to the wobbler irradiation method, a scatterer 601, a collimator 602, and a bolus 603 are additionally disposed inside a beam delivery system 110A.

According to this wobbler irradiation method, a treatment planning system (not illustrated) first selects proper beam energy in accordance with a depth from an irradiation object surface and a size of a target. The beam energy is changed by a method of changing an acceleration condition of the synchrotron 108 or causing the beam to pass through a range shifter (not illustrated) mounted on the beam delivery system 110A. If the beam energy is determined, the thickness of the scatterer 601 is changed in accordance with the size in the lateral direction of the target. Furthermore, a maximum current value supplied from a scanning magnet power supply (not illustrated) to the scanning magnet 203 is determined. The maximum current value determines a radius of a beam scanning path. If beam irradiation starts, beam scanning is circularly performed in the lateral direction. Accordingly, in the scanning magnet power supply, a positive current and a negative current are periodically inverted, and a phase is shifted by 90° for each scanning magnet 203, thereby supplying an AC current equal to the maximum current value, to the scanning magnet 203. Since the beam scanning is circularly performed by using the beam which passes the scatterer and which is dispersed in the lateral direction, a uniform dose distribution is formed in the lateral direction. As means for forming the uniform dose distribution in the lateral direction, it is also an effective way to employ a double scatterer method. According to the double scatterer method, the uniform dose distribution is formed in the lateral direction by arranging two types of scatterer at a beam passing position instead of the scanning magnet.

As illustrated in FIG. 13, a ridge filter 101A employing the wobbler irradiation method is provided with a function to adjust a dispersing range of the beam and to form a spread out Bragg peak (hereinafter, referred to as an SOBP) in the depth direction so as to align with the width of the target 201.

Hereinafter, the ridge filter 101A according to the present embodiment will be described. Similarly to a case of the scanning irradiation method as described in the first embodiment, in each structure 309 configuring a periodic structure of the ridge filter 101A, a sectional shape on a plane vertical to the inward direction is the line symmetry about the line vertical to the depth direction which passes through the center of the structure 309. In addition, the structure 309 has the same shape even if the structure 309 is vertically inverted by a plane vertical to the depth direction. The structure 309 is divided into two small structures 307 by the vertical plane. The small structure 307 according to the present embodiment will be described with reference to FIG. 14.

As illustrated in FIG. 14, the small structure 307 has a step shape in the depth direction, and has a shape in which the spread out Bragg peak is formed in the depth direction. In addition, the small structure 307 has the bilaterally asymmetric shape about the center line in the iterative direction, and has the point symmetric shape about the intersection S between the center line in the iterative direction and the center line in the depth direction. Furthermore, the thicknesses in the iterative direction of an uppermost stream surface 307A and a lowermost stream surface 307B in the depth direction are equal to each other. The structure is configured so that the thick portion in the iterative direction from the uppermost stream surface 307A and the lowermost stream surface 307B in the depth direction is not present.

The bolus 603 and the collimator 602 are processed in advance according to a shape of the target 201. As illustrated in FIG. 12, both of these are attached to a distal end portion of the beam delivery system 110A by an operator. The bolus 603 is formed of an ABS resin, and a range of the beam is adjusted for each place according to the shape of the target 201 in the depth direction. The collimator 602 blocks the beam in a suitable form according to the shape of the target 201 in the lateral direction, thereby reducing beam exposure to the outside of the target 201. The present embodiment employs the collimator 602 which is normally used. However, even if a multi leaf collimator is used, the same advantageous effect can be obtained.

Through the above-described procedure, the uniform dose distribution is formed in the lateral direction and the depth direction of the target 201 by using the wobbler irradiation method.

Other configurations and operations, and a manufacturing method are substantially the same as the configurations and operations, and manufacturing method according to the above-described first embodiment, and thus, details thereof will be omitted.

According to the second embodiment of the particle beam therapy system, the ridge filter, and the manufacturing method of the ridge filter, it is also possible to obtain substantially the same advantageous effect as that according to the above-described first embodiment of the particle beam therapy system, the ridge filter, and the manufacturing method of the ridge filter.

That is, since the ridge filter 101A is a structure having no sharp portion, it becomes easy to perform processing for manufacturing the ridge filter 101A. Therefore, it is possible to inexpensively provide the particle beam therapy system. In particular, in the particle beam therapy system employing the wobbler irradiation method, it is necessary to manufacture many ridge filters in accordance with the energy and the SOBP width. However, in a case of the ridge filter having the structure having no sharp portion as in the present embodiment, the advantageous effect is significantly obtained. In addition, since the processing is facilitated, a higher ridge filter can be manufactured, and a larger SOBP width can be formed. Furthermore, since the ridge filter is less likely to be damaged, an occupancy rate of the particle beam therapy system is improved.

The small structure configuring the structure 309 of the ridge filter 101A according to the present embodiment is not limited to the small structure 307 having the structure in which a triangular pyramid shape having a sharp end whose thickness in the iterative direction as illustrated in FIG. 12 varies in the depth direction is divided by the center line in the iterative direction, and in which a divided one is vertically inverted. The small structure is caused to have a smooth shape in the depth direction as illustrated in FIG. 14. In this manner, it is possible to adopt a small structure 308 having a structure as illustrated in FIG. 15.

The small structure 308 illustrated in FIG. 15 also has the bilaterally asymmetric shape about the center line in the iterative direction, and also has the point symmetric shape about the intersection S between the center line in the iterative direction and the center line in the depth direction. In addition, in the small structure 308, the thicknesses in the iterative direction of the uppermost stream surface 308A and the lowermost stream surface 308B in the depth direction are equal to each other. Furthermore, the uppermost stream surface 308A and the lowermost stream surface 308B in the depth direction have the same thickness. The structure is configured so that the thick portion in the iterative direction is not present in the depth direction. The small structure 308 having this structure can also be manufactured by performing cutting and processing on the ingot formed of aluminum, copper, or ABS, or by using the 3D printer.

According to the ridge filter including the structure configured to include the small structure 308 as illustrated in FIG. 15, it is also possible to obtain the same advantageous effect as that according to the first embodiment.

<Third Embodiment>

As described in the first embodiment, even in a case where the beam is obliquely incident on the ridge filter 101, it is required that a range loss ratio of the beam in the ridge filter 101 does not vary depending on the spot position.

Furthermore, in order to facilitate the processing work and dimensional inspection, it is required that a narrow space is not provided.

Ridge filters 101B and 101C according to the present embodiment will be described with reference to FIGS. 16 and 17. FIGS. 16 and 17 illustrate a schematic cross section of the ridge filter 101 on a plane vertical to the iterative direction according to the present embodiment.

As illustrated in FIG. 16, a structure 701 in the ridge filter 101B has a role corresponding to that of the structure 301 according to the first embodiment and the structure 309 according to the second embodiment.

However, in a shape of the structure 701, similarly to the small structure 305 according to the first embodiment and the small structure 307 according to the second embodiment, the sectional shape on the plane vertical to the inward direction is the bilaterally asymmetric shape about the center line in the iterative direction, and is the point symmetric shape about the intersection S (center of gravity) between the center line in the iterative direction and the center line in the depth direction. The shape of the structure 701 has no mountain-like sharp portion (distal end portion or apex) in the depth direction. The structure 701 is fixed to a fixing portion 702.

In addition, compared to the ridge filter 101 according to the first embodiment or the ridge filter 101A according to the second embodiment, in the ridge filter 101B according to the present embodiment, every other structure 701 is disposed in the iterative direction. Furthermore, a lower surface of the fixing portion 702 includes a structure the same as that of an upper surface. However, the lower surface side includes a structure in which each structure 701 is laterally inverted and a portion corresponding to one structure is shifted in the iterative direction.

As illustrated in FIG. 17, the ridge filter according to the present embodiment may be the ridge filter 101C having a configuration in which the fixing portions 702 are held by being respectively arranged on an upper surface of an upper surface structure 701A and a lower surface of a lower surface structure 701B. In this case, a lower surface of the upper surface structure 701A and an upper surface of the lower surface structure 701B are not necessarily on the same plane.

According to the ridge filter including the structure configured to include the structures 701, 701A, and 701B as illustrated in FIGS. 16 and 17, it is possible to obtain the same advantageous effect as that according to the first embodiment.

<Others>

The invention is not limited to the above-described embodiments, and includes various modification examples. The embodiments have been described in detail in order to facilitate understanding of the invention, and are not necessarily limited by those which include all of the described configurations. In addition, configurations of a certain embodiment can be partially replaced with configurations of the other embodiment. In addition, the configurations of the other embodiment can be added to the configurations of the certain embodiment. In addition, the configurations of each embodiment can partially have additions, omissions, substitutions of other configurations.

For example, according to a ridge filter including a structure in which a plurality of the structures 301 as illustrated in FIG. 7 or a plurality of the structures 309 as illustrated in FIG. 9 are stacked on each other in the depth direction, it is also possible to obtain the same advantageous effect.

In addition, the air layer of the ridge filter 101 may be formed of a material different from that of the structure. For example, the structure may be formed of metal, and a portion corresponding to the gap may be formed of a resin.

REFERENCE SIGNS LIST

101, 101A, 101B, 101C: RIDGE FILTER
102: PROTON BEAM IRRADIATION DEVICE
103: PROTON BEAM GENERATOR
104: PROTON BEAM TRANSFER
105: ROTATING IRRADIATION SYSTEM
106: ION SOURCE
107: PREACCELERATOR
108: SYNCHROTRON
109: EXTRACTION DEFLECTOR
110, 110A: BEAM DELIVERY SYSTEM
201: TARGET
202: SPOT
203: SCANNING MAGNET
301: STRUCTURE OF RIDGE FILTER
301A: UPPERMOST STREAM SURFACE OF STRUCTURE
301B: LOWERMOST STREAM SURFACE OF STRUCTURE
301C: INTERMEDIATE SURFACE OF STRUCTURE
303: BASE PORTION
304: FIXING PORTION
305, 306, 307, 308: SMALL STRUCTURE
305A, 306A, 307A, 308A: UPPERMOST STREAM SURFACE OF SMALL STRUCTURE
305B, 306B, 307B, 308B: LOWERMOST STREAM SURFACE OF SMALL STRUCTURE
601: SCATTERER
602: COLLIMATOR
603: BOLUS
701: STRUCTURE
701A: UPPER SURFACE STRUCTURE
701B: LOWER SURFACE STRUCTURE
702: FIXING PORTION

The invention claimed is:

1. A ridge filter for widening an energy distribution of a particle beam, comprising:
a first structure and a second structure which attenuate energy of the particle beam passing therethrough,
wherein when a particle beam incident direction in the ridge filter is defined as a depth direction, and one direction on a plane vertical to the particle beam incident direction is defined as an iterative direction, in the first structure, a first sectional shape on a plane including a straight line parallel to the depth direction and a straight line parallel to the iterative direction is a point symmetric shape in which the center of gravity of the first sectional shape functions as a symmetric point,
wherein when an uppermost stream side in the depth direction of the first sectional shape is set to a first side and a lowermost stream side in the depth direction of the first sectional shape is set to a second side, the first side and the second side are parallel to each other, and a length of the first side and the second side is longest in the iterative direction,
wherein a quadrangle having the first side and the second side is a parallelogram,
wherein the second structure has a shape in which the first structure is inverted by a plane vertical to the depth direction, and
wherein a plurality of the first structures and the second structures are arranged in the iterative direction.

2. The ridge filter according to claim 1,
wherein the first structure is located on an upstream side from the second structure in the depth direction.

3. The ridge filter according to claim 1, further comprising:
a base portion that fixes the first structure or the second structure on an uppermost stream surface or a lowermost stream surface in the depth direction of the first structure, or on an uppermost stream surface or a lowermost stream surface in the depth direction of the second structure; and
a fixing portion that pinches a plurality of the base portions.

4. The ridge filter according to claim 3,
wherein the ridge filter is an integrally molded product.

5. The ridge filter according to claim 1,
wherein the first structure and the second structure are stacked on each other in the depth direction.

6. The ridge filter according to claim 5,
wherein a second sectional shape on a plane including the first structure and the second structure which are stacked on each other is the same shape as a third sectional shape of a gap on the plane.

7. The ridge filter according to claim 1,
wherein the first structure and the second structure have the same shape when both of these are inverted in the depth direction.

8. The ridge filter according to claim 1,
wherein when viewed in the depth direction, the first structure and the second structure are alternately arranged.

9. A particle beam therapy system comprising;
a ridge filter,
wherein the ridge filter has a first structure and a second structure which attenuate energy of a particle beam passing therethrough,
wherein when a particle beam incident direction in the ridge filter is defined as a depth direction, and one direction on a plane vertical to the particle beam incident direction is defined as an iterative direction, in the first structure, a sectional shape on a plane including a straight line parallel to the depth direction and a straight line parallel to the iterative direction is a point symmetric shape in which the center of gravity of the sectional shape functions as a symmetric point,
wherein when an uppermost stream side in the depth direction of the sectional shape is set to a first side and a lowermost stream side in the depth direction of the sectional shape is set to a second side, the first side and the second side are parallel to each other, and a length of the first side and the second side is longest in the iterative direction,
wherein a quadrangle having the first side and the second side is a parallelogram,
wherein the second structure has a shape in which the first structure is inverted by a plane vertical to the depth direction, and
wherein a plurality of the first structures and the second structures are arranged in the iterative direction.

10. A manufacturing method of a ridge filter for widening an energy distribution of a beam,
wherein the ridge filter has a first structure and a second structure which attenuate energy of a particle beam passing therethrough, wherein when a particle beam incident direction in the ridge filter is defined as a depth direction, and one direction on a plane vertical to the particle beam incident direction is defined as an iterative direction, in the first structure, a sectional shape on a plane including a straight line parallel to the depth direction and a straight line parallel to the iterative direction is a point symmetric shape in which the center of gravity of the sectional shape functions as a symmetric point, wherein when an uppermost stream side in the depth direction of the sectional shape is set to a first side and a lowermost stream side in the depth direction of the sectional shape is set to a second side, the first side and the second side are parallel to each other, and a length of the first side and the second side is longest in the iterative direction, wherein a quadrangle having the first side and the second side is a parallelogram, wherein the second structure has a shape in which the first structure is inverted by a plane vertical to the depth direction, and wherein a plurality of the first structures and the second structures are arranged in the iterative direction.

\* \* \* \* \*